United States Patent [19]
Donnelly et al.

[11] Patent Number: 5,453,077
[45] Date of Patent: Sep. 26, 1995

[54] INFANT THERMAL SUPPORT DEVICE

[75] Inventors: Michael M. Donnelly, Cincinnati, Ohio; Francis J. Buchholz, III; Brent C. Jacobsen, both of Batesville, Ind.

[73] Assignee: Hill-Rom Company, Inc., Batesville, Ind.

[21] Appl. No.: 169,675

[22] Filed: Dec. 17, 1993

[51] Int. Cl.[6] .................................................. A61G 11/00
[52] U.S. Cl. .......................................................... 600/22
[58] Field of Search ........................... 600/21–22; 128/736

[56] References Cited

U.S. PATENT DOCUMENTS

| | | |
|---|---|---|
| 3,158,150 | 11/1964 | Croasdaile . |
| 3,335,713 | 8/1967 | Grosholz et al. . |
| 3,387,600 | 6/1968 | Terzian . |
| 3,511,162 | 5/1970 | Truhan . |
| 3,618,734 | 11/1971 | Khan . |
| 3,776,217 | 12/1973 | van Galen et al. . |
| 3,782,362 | 1/1974 | Puzio . |
| 3,821,947 | 7/1974 | Schossow . |
| 3,858,570 | 1/1975 | Beld et al. ................. 600/22 |
| 4,063,495 | 12/1977 | Duvlis . |
| 4,140,105 | 2/1979 | Duvlis . |
| 4,321,913 | 3/1982 | Maluta et al. . |
| 4,361,137 | 11/1982 | Grosholz . |
| 4,423,669 | 1/1984 | Bullock et al. . |
| 4,617,912 | 10/1986 | Beer et al. . |
| 4,750,474 | 6/1988 | Dukhan et al. . |
| 4,809,677 | 3/1989 | Mackin et al. . |
| 4,846,783 | 7/1989 | Koch et al. . |
| 4,936,824 | 6/1990 | Koch et al. . |
| 5,162,038 | 11/1992 | Wilker . |
| 5,308,310 | 5/1994 | Roff et al. ................. 600/21 |

FOREIGN PATENT DOCUMENTS

| | | |
|---|---|---|
| 0236851 | 2/1987 | European Pat. Off. . |
| 2031559 | 11/1970 | France . |
| 2061704 | 7/1979 | Germany . |
| 3607575 | 9/1987 | Germany . |
| 122184 | 11/1974 | Japan . |
| 2175213 | 11/1986 | United Kingdom . |
| 9009771 | 9/1990 | WIPO ................................ 600/22 |

OTHER PUBLICATIONS

Dec. 1971 Journal of Pediatrics "Air Curtain Incubator for use in an Intensive–Care Nursery", Musch, Adams and Sunshine, vol. 79, No. 6, pp. 1024–1030.
Infa–Care 2000, 1972.

Primary Examiner—William E. Kamm
Assistant Examiner—John P. Lacyk
Attorney, Agent, or Firm—Barnes & Thornburg

[57] ABSTRACT

An infant thermal support device which provides convective heat transfer similar to an incubator yet which allows for unlimited care provider access to the infant without compromising the infant's thermal environment. The device has an infant support with head and foot ends and lateral sides, and provides a heated curtain of air traveling over an infant on the support to maintain the temperature of the infant at an appropriate level. Vertically oriented curtains of air travel upwardly from the lateral edges and at least one end of the support. The device provides warmth to the infant on the support by virtue of the heated air curtain, and the vertically oriented air curtains reduced perturbations of the heated air curtain caused by physical disturbances adjacent to the device such that a canopy enclosing the device is not required. The device further comprises a raisable and lowerable canopy and infrared heater, such that the device can function as either an infant radiant warmer, an incubator or both. Sensors mounted on the device sense disturbances around the device and the position of the canopy and vary the speeds of the heated air curtain and perturbation reducing curtains accordingly.

28 Claims, 6 Drawing Sheets

INFANT THERMAL SUPPORT DEVICE

FIELD OF THE INVENTION

This invention relates generally to neonatal patient treatment devices, and more particularly to a thermal support device for maintaining appropriate temperature of an infant.

BACKGROUND OF THE INVENTION

Incubators and radiant warmers have both been used to maintain the appropriate body temperature of small or premature infants. An incubator provides an enclosure, generally transparent, within which heated air is circulated to minimize heat loss of the infant. Heat is transferred to the infant via convective heat transfer. A major drawback of the typical incubator is that it provides for only limited access by a care provider to the infant. More particularly, the incubator typically provides a large access door for placing the infant into or removing the infant from the incubator. However, it will be appreciated that opening such a door causes rapid cooling of the interior of the incubator, and therefore should be opened as seldom as possible in order to maintain the appropriate temperature of the incubator interior and hence the infant. Thus, most incubators are provided with means of supplemental access in the form of hand ports or small entry doors for routine care of the infant to minimize heat loss during care of the infant. Such small entry doors and hand ports, however, are quite limiting in that a care provider does not have complete access to and mobility with respect to an infant within the incubator.

Radiant warmers, on the other hand, provide for continuous and open access to an infant to accommodate a high frequency of care provider intervention. In radiant warmers heat is transferred to the infant via radiative heat transfer. Radiant warmers typically include infrared heaters which emit infrared energy which is absorbed by the skin of the infant. The infrared heater is typically mounted to a support which is suspended above the infant support surface of the radiant warmer. There is no canopy or enclosure as in incubators. Radiant warmers thus provide open access to infants requiring surgery, for example, or other procedures requiring multiple care providers to have access to and unobstructed sight of the infant. However, while incubators are typically provided with humidification mechanisms to raise the level of relative humidity within the incubator, thus contributing to a reduction in heat loss from evaporation of fluids from the infant, radiant warmers due to their open nature and the mode of heat transfer employed cause infant evaporative water losses which are significantly greater than those encountered by an infant within an incubator. Another disadvantage of the radiant warmer, when compared to an incubator, is that the infant is directly exposed to ambient nursery contaminants in the form of noise and unfiltered air. The incubator, on the other hand, being an enclosure for the infant, reduces the effects of nursery environmental conditions on the infant.

SUMMARY OF THE INVENTION

It has therefore been an objective of the present invention to improve upon prior art incubators by providing an incubator which will maintain the appropriate temperature of a premature infant via convective heat transfer yet which will also increase caregiver access to the infant.

It has been another objective of the present invention to combine the advantages of each of the prior art types of incubators and radiant warmers into a single infant warming device, which combination exploits the advantages of each of these two types of prior art devices but as well avoids the inherent disadvantages in them when employed singly.

In accordance with the objectives of the present invention and a preferred embodiment thereof, the present invention comprises, in its broadest form, an infant thermal support device providing convective heat transfer to the infant similar to an incubator, yet which allows for unlimited care provider access to an infant, and without compromising the infant's thermal environment. The invention provides an infant support having head and foot ends and lateral sides, with the support providing a heated curtain of air traveling over an infant on the support to maintain the temperature of the infant's skin at an appropriate level. The support provides curtains of air traveling upwardly from the lateral sides and at least one of the ends of the support. The warming device provides warmth to the infant on the support by virtue of the heated air curtain, and the upwardly oriented air curtains reduce perturbations of the heated air curtain caused by physical disturbances adjacent the device such that the device does not require a canopy enclosing the device to maintain the infant warm. Thus, the device provides unlimited caregiver access to an infant supported on the support, while maintaining the appropriate temperature of the infant by a convective mode of heat transfer.

The device in its preferred form provides three infant thermal environment controlling air curtains, and at least three air curtains protecting the three thermal environment air curtains from perturbations due to physical disturbances adjacent to the device. The first heated air curtain travels from the foot end of the infant support toward the head end of the infant support over an infant supported by the support, at a velocity of up to approximately 0.1 meters per second and temperature of up to about 38°–39° C. The second and third heated air curtains travel from the lateral edges of the support upwardly and toward one another at approximately 45° angles relative to the support and over the infant supported by the support, at a velocity of up to approximately 0.5 meters per second and temperature of up to approximately 38°–39° C.

The three air curtains which prevent perturbations of the heated air curtains from physical disturbances travel upwardly preferably vertically from the lateral sides and the foot end of the support at a velocity of approximately 1–2 meters per second.

The infant warming device further preferably comprises a canopy mounted over the infant support and adapted to be raised and lowered relative to the support, such that the canopy can be lowered to a lowermost position which substantially encloses the support. The device can then function, with canopy lowered, as a traditional enclosed incubator. With the canopy raised to provide complete and unrestricted access to the infant, the three heated air curtains and three perturbation-reducing air curtains maintain the infant thermal environment.

The device of the present invention further preferably provides an infrared heater mounted above the support and which is adapted to be raised and lowered relative to the support along with the canopy. The device, in this form, is in essence a combination infant radiant warmer and incubator. Thus, the device can function as either a traditional incubator, a traditional radiant warmer, or can function simultaneously as both, with the raisable and lowerable canopy, heated air curtains and perturbation-reducing air curtains and infrared heater maintaining the thermal environment of the infant as desired.

Another feature of the present invention is a heated shelf storage area on the infant support portion of the warmer for storing various items such as probes, probe covers and laryngoscopes.

Yet another feature of the present invention is the provision of a canopy including a light reduction medium for selected darkening of the infant sleep area of the warmer.

A further feature of the present invention is the provision of a motion sensor mounted on the infant support for sensing disturbances around the infant thermal support device, and a controller for controlling the speed of the fan which provides the curtains of air traveling upwardly. The controller, upon the sensor sensing a disturbance, is operable to increase the speed of the fan providing those curtains of air traveling upwardly to further reduce perturbations of the heated air curtain or curtains.

Still a further feature of the present invention is the provision of a position sensor associated with the raisable and lowerable canopy for determining the relative position of the canopy relative to the infant support, and a controller which, upon the sensor sensing the relative position of the canopy with respect to the support, is operable to decrease the speed of the fan providing the upwardly traveling air curtains as the need for those upwardly traveling air curtains diminishes as the canopy is lowered and approaches the infant support, and to decrease the speed of the fan providing the heated air curtains as the need for the heated air curtains diminishes due to the infant becoming substantially enclosed by the support and canopy.

The present invention provides numerous advantages over traditional incubators and radiant warmers, one of which is that the device provides an infant thermal environment very nearly identical to that provided by a traditional incubator, yet which provides totally unrestricted and unlimited access to the infant by a care provider, unlike traditional incubators.

Another advantage of the present invention is that it combines the benefits of both traditional incubators and radiant warmers into a single device, thus exploiting the advantages of both while tending to eliminate the disadvantages when employing either singly.

These and other objects and advantages of the present invention will become more readily apparent during the following detailed description taken in conjunction with the drawings herein, in which:

DETAILED DESCRIPTION OF THE INVENTION

Figure 1:
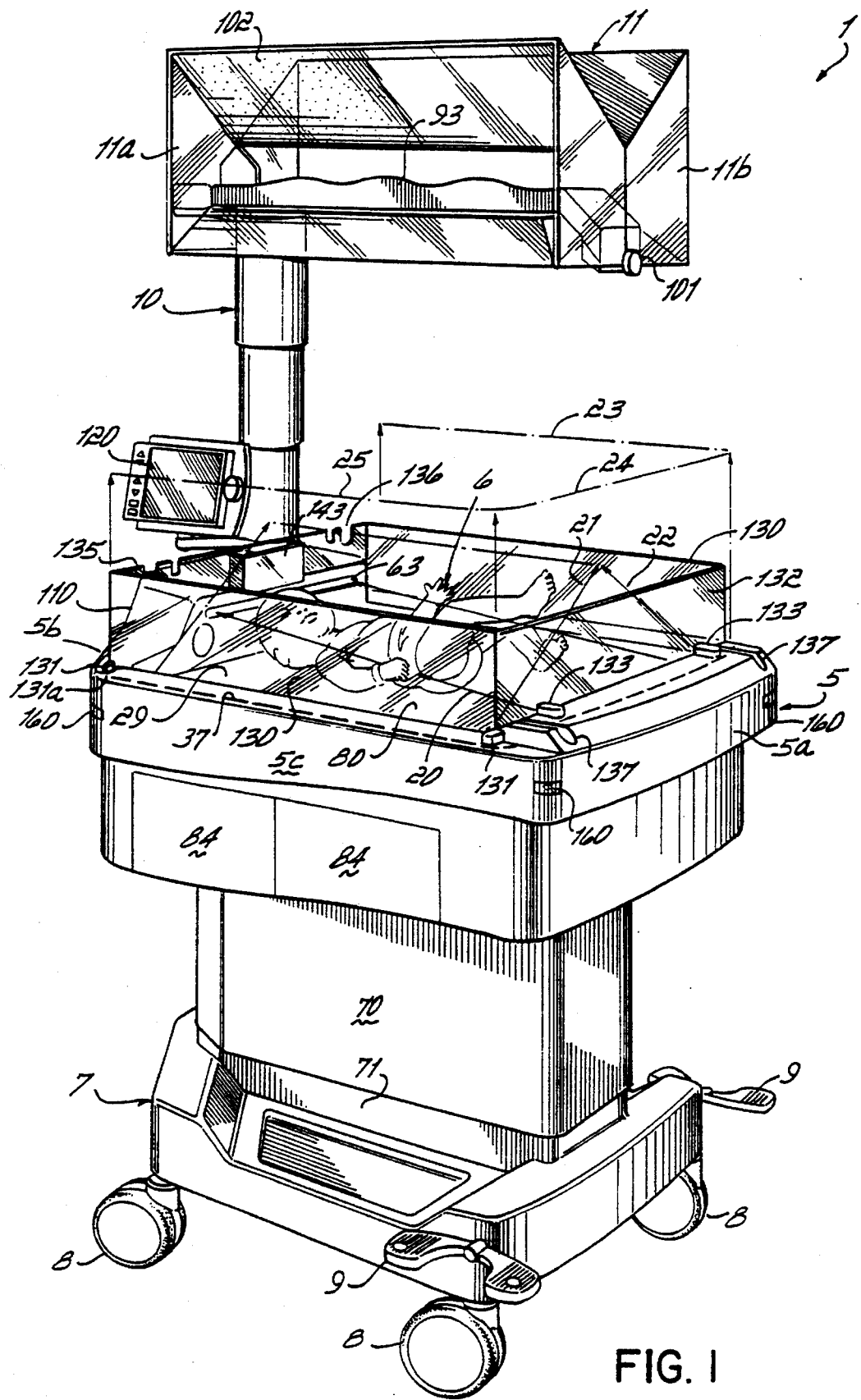
FIG. 1 is a perspective view of the infant warming device of the present invention.

With reference first to FIG. 1, there is illustrated the infant warming device 1 of the present invention. The device 1 includes, generally, an infant supporting portion 5 for supporting an infant 6, a base portion 7 having castors 8 and brake/steer pedals 9, and a canopy support arm 10 supporting a canopy 11.

Figure 2:
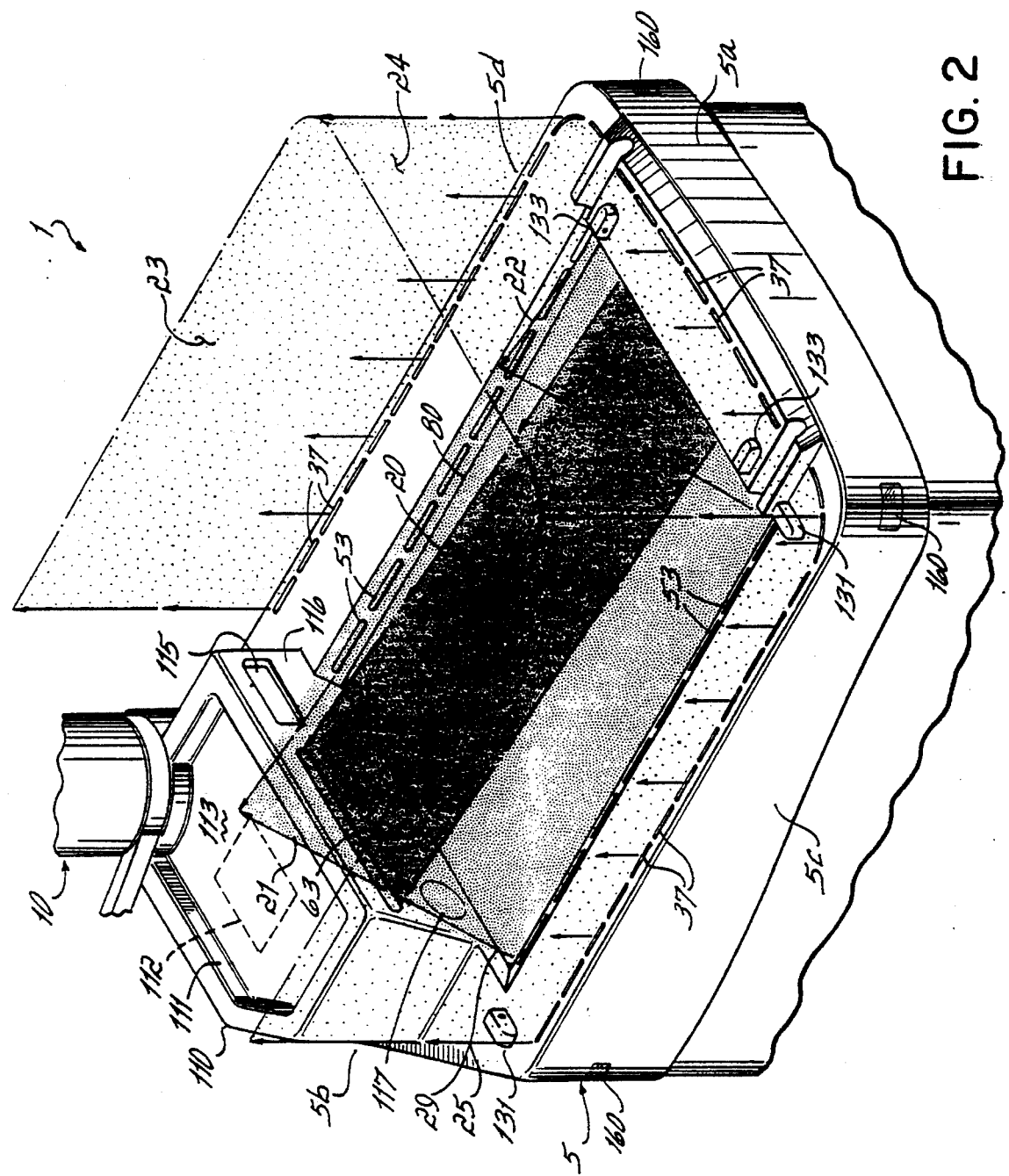
FIG. 2 is an enlarged perspective view of the air curtain scheme of the present invention.
Figure 3:
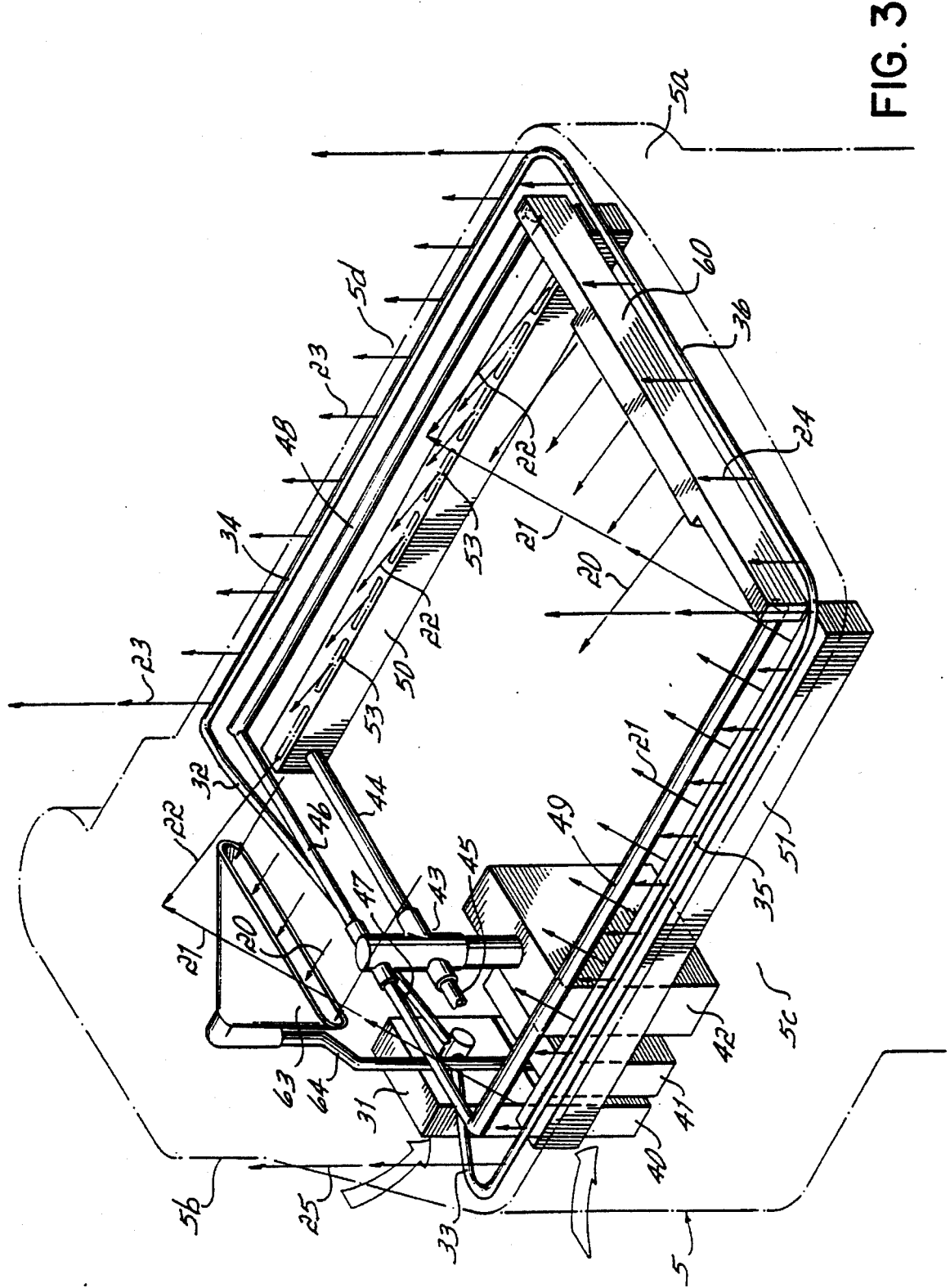
FIG. 3 is a view similar to FIG. 2 but illustrating the pneumatic circuitry for providing the air curtain scheme.

Referring to FIGS. 1 and 2, the infant warming device 1 of the present invention, in its preferred form, provides three heated air curtains 20, 21 and 22, and three additional air curtains 23, 24 and 25. More particularly, heated air curtain 20 travels from the foot end 5a towards the head end 5b of infant support 5 and over an infant 6 supported thereby closely adjacent the infant. Air curtains 21 and 22 travel upwardly from lateral sides 5c and 5d of patient support 5 upwardly toward one another and over the infant 6 supported by the support. The curtains 21 and 22 each preferably form an angle of approximately 45° with respect to the supporting surface 29 of the infant support 5. Supporting surface 29 defines an infant platform area approximately 26.25 inches long and 17.5 inches wide. Air curtain 20 preferably has a velocity of up to approximately 0.1 meters per second and a temperature of up to approximately 38°–39° C., while air curtains 21 and 22 each preferably have a velocity of up to approximately 0.5 meters per second and a temperature of up to approximately 38°–39° C. Air curtains 23, 24 and 25 have a velocity of approximately 1–2 meters per second and preferably are oriented generally vertically.

Referring to FIGS. 1–5, and describing the air flow system of the infant warming device 1 of the present invention in more detail, at the lower head end 5b of the patient support portion 5 of the device 1 there is an intake or grill 30 for drawing in ambient air from the surroundings. A fan 31 supplies air to conduits or passages 32 and 33 which connect with passages 34, 35 and 36 in the lateral sides 5c, 5d and foot end 5a, respectively, of the patient support 5. Slots 37 allow air to escape from the passages 34, 35 and 36, and thus forming the vertical, upwardly traveling air curtains 23, 24 and 25. Slots 37 are approximately 2 inches long and 0.062 inches wide.

Another fan 40 likewise receives ambient air from air intake or grill 30 and supplies it to a filter 41. The filtered air then passes through a humidifier 42 and on into a manifold 43 which channels air through two sets of conduits or passages, 44, 45 and 46, 47. Conduits or passages 44, 45 channel air to rectangular passageways 50, 51 respectively, within the lateral sides 5d, 5c respectively of support portion 5 of the device 1. The air passing through passageways 50, 51 is heated by heaters 52 on the floor of each passageway, and exits slots 53 thus forming air curtains 21 and 22. It will be appreciated though that heaters 52 could be positioned at locations other than the floor of the passageway. Slots 53 are approximately 3 inches long, 0.375 inches wide and 2 inches deep. The approximate distance between the slots 53 across the lateral dimension of the support 5 is approximately 18 inches. Air curtains 21 and 22 converge above patient support surface 29 at an approximate distance ranging from 9 to 14 inches.

Conduits or passages 46 and 47 supply a rectangular, though other cross-sections may be employed, passageway 60 in the foot end 5a of the support portion 5 of the device 1. Air passing through passageway 60 is heated by heater 61 (FIG. 4) on the floor of that passageway, though other locations for heater 61 may be employed. The heated air exits slots 62 and travels from the foot end 5a to the head end 5b and enters intake 63 in the head end 5b of the support 5. Return air is channeled through conduit 64 downwardly and back into the air circuit upstream of filter 41. Slots 62 are generally the same dimensions as slots 53; slots 62 are located approximately in the same horizontal plane as slots 53. Intake 63 is approximately 0.5 inches wide and 9 inches long, and is located approximately 2.75 inches above the horizontal plane of slots 53 and 62.

Figure 4:
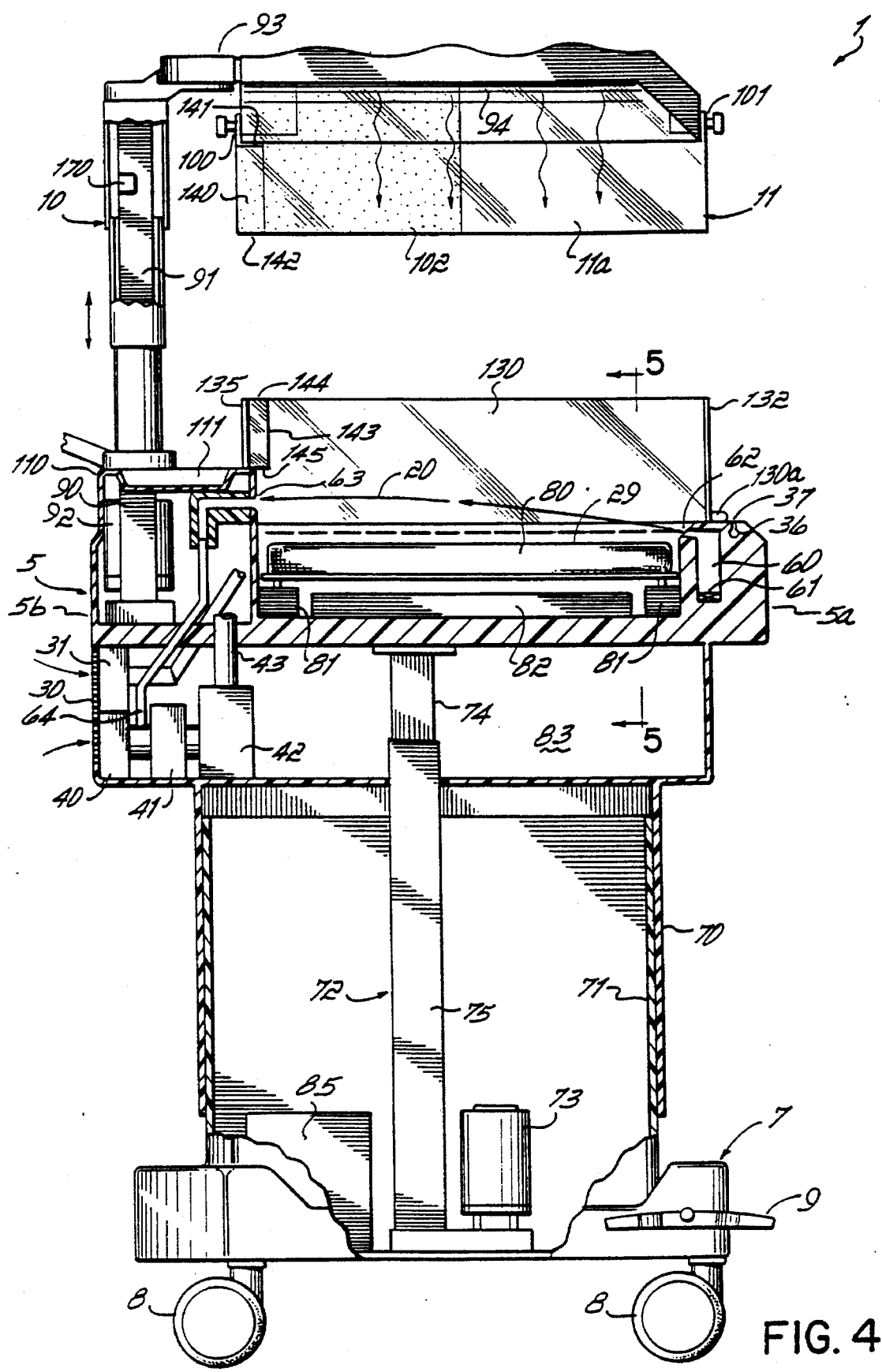
FIG. 4 is a side elevational view, in partial cross-section, of the device with canopy raised and in traditional IR warmer mode.

Referring to FIG. 4, it will be seen that patient support portion 5 includes a depending rectangular tubular portion 70 which slidably cooperates with an upwardly extending portion 71 of the base 7. A vertical drive 72 powered by motor 73 includes a piston portion 74 and a cylinder portion 75, the piston portion 74 for extending out of and retracting into the cylinder portion 75 and for raising and lowering the patient support portion 5.

Patient support surface 29 is essentially the top surface of an infant supporting mattress 80, either end of which is supported on weight scales or the like 81 for monitoring weight of an infant 6 supported thereon. An x-ray cartridge or the like 82 may be inserted underneath mattress 80 for x-raying of the infant 6. A storage area 83 underlying cartridge 82 provides additional storage and may be accessed by drawers 84.

An uninterrupted power supply 85 powers the fans and heaters of the air system during, for example, mobile transport of the device 1 when AC wall power is not available.

Canopy support arm 10 includes a piston portion 90 and a cylinder portion 91 powered by a motor 92 for raising and lowering of a horizontal portion 93. Horizontal portion 93 of canopy support arm 10 includes an infrared heater 94 on an underside thereof, and has mounted thereto the canopy 11. Canopy 11 includes two halves 11a and 11b which are hinged together and connected to the horizontal portion 93 of canopy support arm 10 at 100 and 101. The canopy halves 11a and 11b are rotatable through 90° upwardly to the configuration shown in FIG. 1, and downwardly through 90° to the configuration shown in FIG. 6. The pivoting canopy halves 11a and 11b thus provide additional access to infant 6 by care providers in addition to the access had by the raising and lowering of the canopy 11 by canopy support arm 10. Canopy halves 11a and 11b are preferably fabricated of transparent material, e.g., plexiglass. All or a portion of canopy 11, for example the head end portion of the canopy halves 11a, 11b as shown, includes a light reduction medium, for example a liquid crystal light shutter shown at 102, which allows selective darkening of the infant sleep surface.

Referring to FIG. 2, the head end 5b of the support portion 5 of the device 1 includes a raised portion 110 which includes a recessed area 111 therein. The recessed area 111 is designed as a shelf or storage area for storing various items, such as probes, probe covers, laryngoscopes, and resuscitation masks. This storage area 111 is preferably heated by placing a heating element or source as shown at 112 underneath the surface 113 of the storage area 111, thus heating the items stored thereon such that when those items come in contact with the infant 6 the infant is not startled or otherwise traumatized due to their otherwise cold nature. Raised area 110 further includes another storage area 115 in the rear vertically oriented face 116 of the raised structure 110 and is suitable for storage of probe wires, etc. Additionally, a speaker 117 is provided on face 116 of the structure 110 for directing suitable calming audible input into the infant's environment.

A combination controller and display 120 (FIGS. 1 and 6) is provided for controlling the motors 73 and 92 of the infant support 5 and canopy 11 drives, respectively, as well as blowers 31 and 40, heaters 52, 61 and 112, and light shutter 102, and for displaying patient data.

Figure 5:
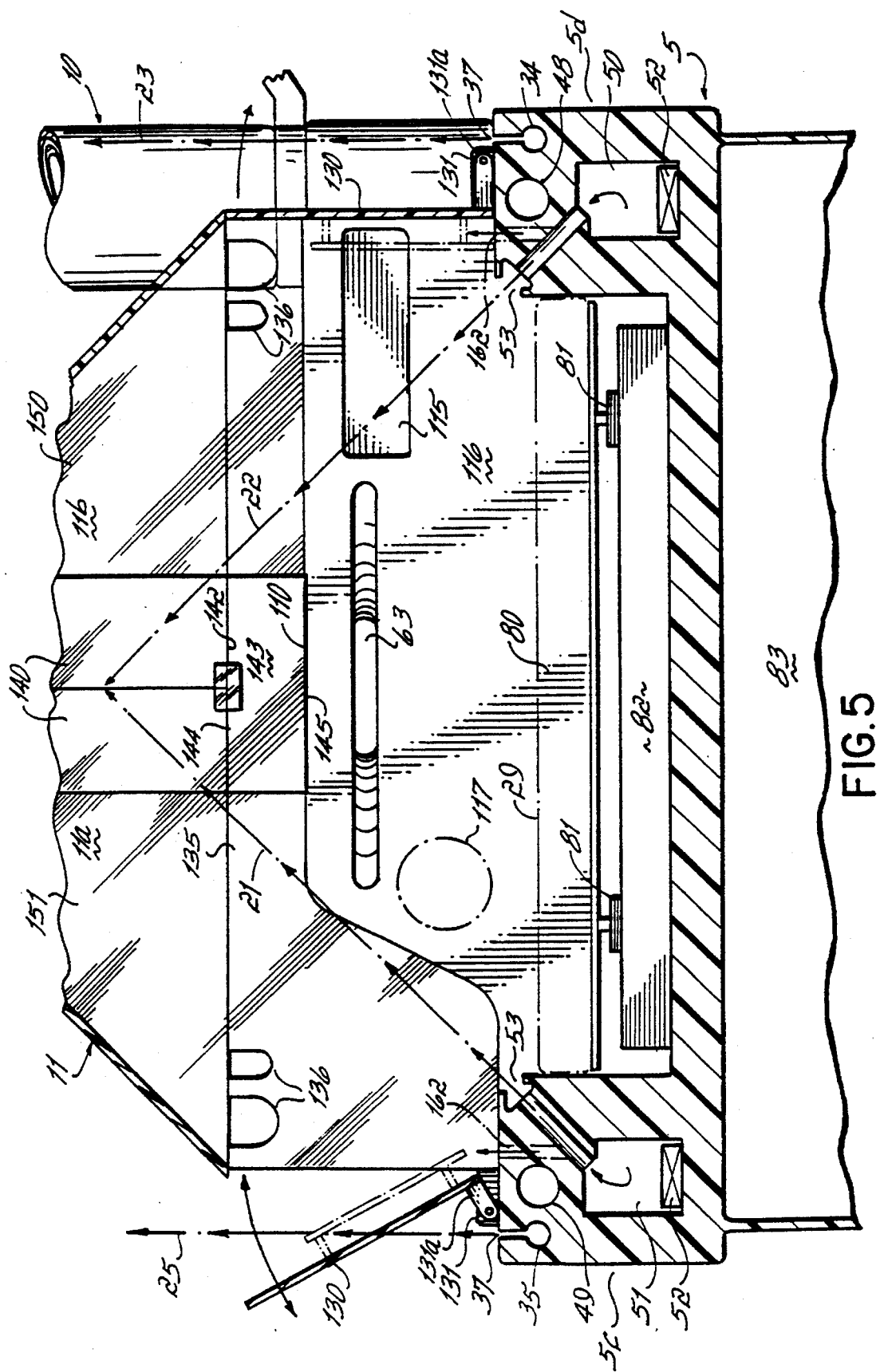
FIG. 5 is a view of the device taken along line 5—5 of FIG. 4 but with canopy lowered and in traditional incubator mode.
Figure 6:
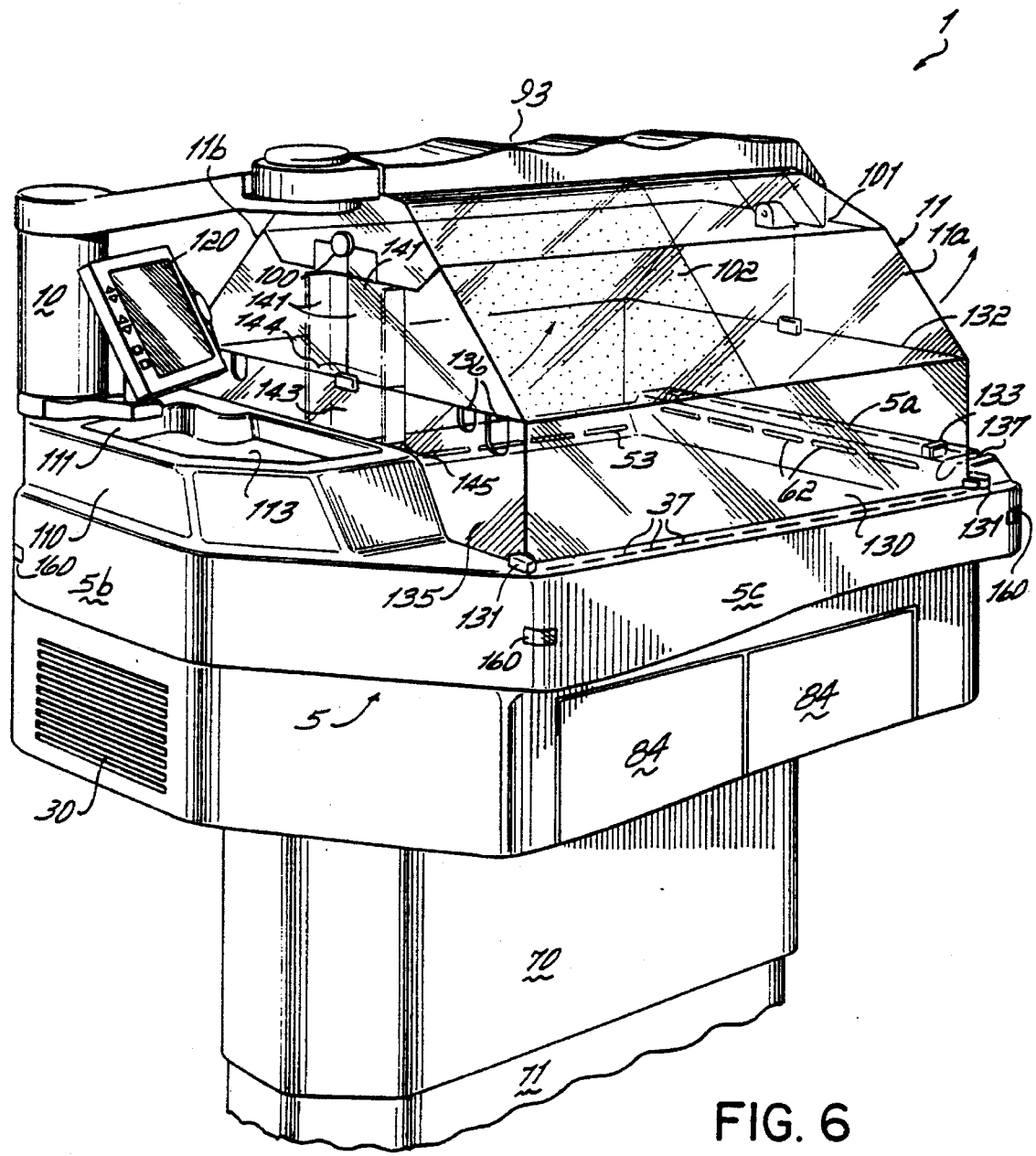
FIG. 6 is a perspective view of the device in traditional incubator mode.

Referring to FIGS. 1 and 6, transparent sideguards 130 fabricated of, e.g., plexiglass, are pivoted at either end by pivot joints 131 offset from respective sideguards 130 by offset arms 131a and may be pivoted downwardly (FIG. 5) to provide for increased access to infant 6. Similarly, a transparent footguard 132 likewise fabricated of, e.g., plexiglass, is similarly pivoted on its ends by pivot joints 133 offset from footguard 132 by offset arms (not shown) and may be pivoted downwardly for increased access. Due to their offset arms, sideguards 130 and footguard 132 provide unrestricted air flow from slots 37 for the air curtains 23, 24 and 25 whether the guards are up or down. At the head end of the support 5 an additional transparent panel 135 of, e.g., plexiglass, is removably secured there, as by slidably mounting within grooves (not shown), and is removable as well. Notches 136 in the upper edge of panel 135 near its corners provide for various life supporting lines to be run into the environment of the infant 6, as do notches 137 in the lateral edges of the foot end 5a of the support 5.

Referring to FIG. 6, it will be seen that when the canopy halves 11a, 11b are rotated downwardly, and when the canopy support arm 10 is driven downwardly by motor 92, the lower edges of the canopy support halves 11a, 11b engage with the upper edges of the guards 130, 130, 132, 135. The canopy 11 and infant support 5 thus form a substantial enclosure, essentially duplicating a traditional incubator.

To further enhance the efficiency of the thermal support device 1 of the present invention, and referring now to FIGS. 4–6, a convective air return slot 140 is incorporated into each of the head end panels 150, 151 of the canopy halves 11a and 11b. The convective air return slots are open at their upper ends 141. When the canopy halves are pivoted downwardly into the configuration shown in FIG. 6, the slots 140 in each of the panels 150, 151 come together to form a channel or passage having the above-described upper opening 141 and a lower opening 142. Head end panel 135 of support 5 likewise includes a similar convective return slot 143 having an upper opening 144 and a lower opening 145 forming a similar channel or passageway in the head end panel 135. When the canopy 11 is lowered onto the upper edges of the guards 130, 130, 132, 135 (FIG. 6), the lower opening 142 of passage 140 abuts the upper opening 144 of passage 143. Heated air from the air curtains 21 and 22 will be drawn into opening 141 and will pass downwardly through passages 140, 143 and into return or intake 63. Passages 140, 143 thus increase the efficiency of the convective air curtains 21 and 22 by recirculating heated air from those air curtains back through the pneumatic circuitry. An additional benefit of such a return is that it provides a means of cooling or reducing the heater 94 temperature mounted on the underside of canopy support arm 10 by convective cooling of the heater surface when the canopy is in a closed position.

Referring now to FIGS. 1, 2 and 6, a sensor 160 is mounted to each of the four corners of the infant supporting portion 5 of the device 1. The purpose of the sensors is to detect perturbations caused by the movement of care personnel and equipment around the device 1. When a sensor 160 is activated, it relays the disturbance information to the controller 120; the controller 120 then increases the speed of fan 31 hence increasing the velocity of the vertical air curtains 23, 24 and 25 to further increase the resistance of the heated air curtains 20, 21 and 22 to perturbations caused by the sensed physical disturbances. When the sensors 160 no longer sense the physical disturbance, the controller 120 would reduce the speed of the blower or fan 31 down to a lower nominal speed. Preferably the sensors would have a sensitivity detection adjustment range of approximately 3-6 ft. around the device 1.

To avoid heat loss from the infant thermal environment to the sideguards 130, a portion of the air curtains 21 and 22 is bled off to heat the sideguards 130. Referring to FIG. 5, slots 162 (phantom) are included within the portion 5 of the device 1 which communicate with the slots 53 which form the air curtains 21 and 22. Heated air exiting the slots 162 is directed upwardly along the interior faces of the side panels 130. Alternatively, the sideguards 130 could be of double wall construction (phantom), wherein the air exiting the slots 162 is directed between the inner and outer walls of the sideguards 130. Yet another method for warming the sideguards 130 would be to incorporate electrical strip heaters (not shown) within or on the sideguards 130.

Referring to FIG. 4, a position sensor 170 is incorporated within canopy support arm 10 to sense the position of the canopy 11 relative to the support 5. Controller 120 is operable, upon receiving input from sensor 170, to vary the speed of various ones of the fans and hence air curtains 20-25. As discussed previously, with the canopy raised, the air curtain 20 would have a velocity of up to approximately 0.1 meters per second, the air curtains 21 and 22 would have velocities up to approximately 0.5 meters per second and the air curtains 23-25 would have velocities up to approximately 1-2 meters per second. With the canopy 11 lowered atop the guards 130, 130, 132, 135 the sensor 170, sensing the lowered position of the canopy, would relay this information to the controller 120 which would adjust the speeds of the air curtains accordingly. With the canopy 11 in the lowered position, the need for the perturbation reducing curtains 23-25 diminishes or is obviated, and less heated air from the heated air curtains 20-22 is required to maintain warmth of the infant since the infant is substantially enclosed by canopy 11. The speed of the air curtain 20 would remain unchanged, whereas the speeds of the air curtains 21 and 22 would be reduced so as to range up to 0.1-0.2 meters per second, and the speeds of the air curtains 23-25 would be reduced so as to range up to 0.5 meters per second or less.

In use, the infant thermal support device of the present invention provides the convective heat transfer and humidification benefits of a traditional incubator, but allows totally unrestricted and complete access to an infant by the care provider. Upon placing the infant within the device, the sideguards can be installed in their upright configurations for safety. The hinged halves of the canopy can be pivoted upwardly, and the entire canopy can be raised upwardly, both offering complete access to the infant. The heated air curtains in effect provide a heated warm air canopy about the infant, while the upwardly oriented high speed air curtains reduce or prevent physical disturbances from creating perturbations in the three heated air curtains. Alternatively, the canopy halves can be pivoted downwardly, and the entire canopy lowered such that the canopy substantially encloses the infant support, as in traditional incubators. In this manner, the device can function as a traditional incubator.

Additionally, the device can function as a traditional radiant warmer by activating the infrared heater mounted in the canopy support arm. In this configuration, the canopy would be raised upwardly to its uppermost position. Should supplemental heating be required or desired, one or more of the heated air curtains can be activated, as well as the perturbation-reducing high speed vertical air curtains, to provide the appropriate amount of heat and humidity.

Those skilled in the art will readily recognize numerous adaptations of modifications which can be made to the infant thermal support device of the present invention which will result in an improved infant thermal support device, yet all of which will fall within the spirit and scope of the present invention as defined in the following claims. Accordingly, the invention is to be limited only by the following claims and their equivalents.

What is claimed is:

1. An infant thermal support device comprising:

an infant support having head and foot ends and lateral sides;

means for providing at least one heated curtain of air traveling over an infant on said support; and means for providing curtains of air traveling upwardly from said lateral sides and at least one of said head and foot ends of said support;

whereby said at least one heated air curtain provides warmth to the infant on said support and said upwardly oriented air curtains tend to reduce perturbations of said at least one heated air curtain due to physical disturbances near said device thus providing an infant thermal support device which does not require a canopy enclosing said device to maintain the infant warm.

2. The infant thermal support device of claim 1 wherein said at least one heated curtain of air comprises a heated air curtain traveling from one of said head and foot ends of said support toward the other of said head and foot ends of said support and over an infant supported by said support.

3. The infant thermal support device of claim 1 wherein said at least one heated curtain of air comprises a pair of heated air curtains traveling from said lateral sides of said support upwardly and toward one another over an infant supported by said support.

4. The infant thermal support device of claim 1 wherein said at least one heated curtain of air comprises:

a first heated air curtain traveling from one of said head and foot ends of said support toward the other of said head and foot ends of said support over an infant supported by said support; and second and third heated air curtains traveling from said lateral sides of said support upwardly and toward one another and over an infant supported by said support.

5. A combination infant radiant warmer and incubator thermal support device comprising:

an infant support;

a canopy mounted over said support and adapted to be raised and lowered relative to said support, said canopy when lowered to a lowermost position substantially enclosing said support;

an infrared heater mounted over said support and adapted to be raised and lowered relative to said support along with said canopy; and means for providing a heated curtain of air from said infant support traveling over an infant on said support;

whereby said device is operable to function as a radiant warmer with said canopy raised above said support and said heater activated, and is operable to function as an incubator with said canopy lowered onto said support and said means for providing a heated air curtain activated.

6. A combination infant radiant warmer and incubator thermal support device comprising:

an infant support having head and foot ends and lateral sides;

a canopy mounted over said support and adapted to be raised and lowered relative to said support, said canopy when lowered to a lowermost position substantially enclosing said support;

an infrared heater mounted over said support and adapted to be raised and lowered relative to said support along with said canopy;

means for providing at least one heated curtain of air traveling over an infant on said support; and means for providing curtains of air traveling upwardly from said lateral sides and at least one of said head and foot ends of said support;

whereby said device is operable to function as a radiant warmer with said canopy raised above said support and said heater activated, and is operable to function as an incubator with said canopy lowered onto said support and said means for providing at least one heated air curtain activated, and whereby said upwardly oriented air curtains tend to reduce perturbations of said at least one heated air curtain due to physical disturbances near said device when said canopy is raised above said support.

7. The combination infant radiant warmer and incubator thermal support device of claim 6 wherein said at least one heated curtain of air comprises a heated air curtain traveling from one of said head and foot ends of said support toward the other of said head and foot ends of said support and over an infant supported by said support.

8. The combination infant radiant warmer and incubator thermal support device of claim 6 wherein said at least one heated curtain of air comprises a pair of heated air curtains traveling from said lateral sides of said support toward one another over an infant supported by said support.

9. The combination infant radiant warmer and incubator thermal support device of claim 6 wherein said at least one heated curtain of air comprises:

a first heated air curtain traveling from one of said head and foot ends of said support toward the other of said head and foot ends of said support over an infant supported by said support; and second and third heated air curtains traveling from said lateral sides of said support upwardly and toward one another and over an infant supported by said support.

10. An infant thermal support device comprising:

an infant support having head and foot ends and lateral sides;

at least one fan and at least one heater providing at least one heated curtain of air traveling over an infant on said support; and a fan providing curtains of air traveling upwardly from said lateral sides and at least one of said head and foot ends of said support;

whereby said at least one heated air curtain provides warmth to the infant on said support and said upwardly oriented air curtains tend to reduce perturbations of said at least one heated air curtain due to physical disturbances near said device thus providing an infant thermal support device which does not require a canopy enclosing said device to maintain the infant warm.

11. The infant thermal support device of claim 10 wherein said at least one heated curtain of air comprises a heated air curtain traveling from one of said head and foot ends of said support toward the other of said head and foot ends of said support and over an infant supported by said support.

12. The infant thermal support device of claim 10 wherein said at least one heated curtain of air comprises a pair of heated air curtains traveling from said lateral sides of said support upwardly and toward one another over an infant supported by said support.

13. The infant thermal support of claim 10 wherein said at least one heated curtain of air comprises:

a first heated air curtain traveling from one of said head and foot ends of said support toward the other of said head and foot ends of said support over an infant supported by said support; and second and third heated air curtains traveling from said lateral sides of said support upwardly and toward one another and over an infant supported by said support.

14. The infant thermal support device of claim 11 wherein said curtains of air traveling upwardly from said lateral sides and at least one of said head and foot ends of said support are generally vertically oriented, and wherein said heated air curtain travels over the infant closely adjacent the infant.

15. The infant thermal support device of claim 12 wherein said curtains of air traveling upwardly from said lateral sides and at least one of said head and foot ends of said support are generally vertically oriented, and wherein said pair of heated air curtains each form an angle of approximately 45° with respect to said support.

16. The infant thermal support of claim 13 wherein said curtains of air traveling upwardly from said lateral sides and at least one of said head and foot ends of said support are generally vertically oriented, said first heated air curtain travels over the infant closely adjacent the infant, and said second and third heated air curtains each form an angle of approximately 45° with respect to said support.

17. A combination infant radiant warmer and incubator thermal support device comprising:

an infant support;

a canopy mounted over said support and adapted to be raised and lowered relative to said support, said canopy when lowered to a lowermost position substantially enclosing said support;

an infrared heater mounted over said support and adapted to be raised and lowered relative to said support along with said canopy; and at least one fan and at least one heater providing heated air from said infant support traveling over an infant on said support;

whereby said device is operable to function as a radiant warmer with said canopy raised above said support and said heater activated, and is operable to function as an incubator with said canopy lowered onto said support and said fan and heater providing a heated air curtain activated.

18. A combination infant radiant warmer and incubator thermal support device comprising:

an infant support having head and foot ends and lateral sides;

a canopy mounted over said support and adapted to be raised and lowered relative to said support, said canopy when lowered to a lowermost position substantially enclosing said support;

an infrared heater mounted over said support and adapted to be raised and lowered relative to said support along with said canopy;

at least one fan and at least one heater providing at least one heated curtain of air traveling over an infant on said support;

a fan providing curtains of air traveling upwardly from said lateral sides and at least one of said head and foot ends of said support;

whereby said device is operable to function as a radiant warmer with said canopy raised above said support and said infrared heater activated, and is operable to function as an incubator with said canopy lowered onto said support and said fan and heater providing at least one heated air curtain activated, and whereby said upwardly oriented air curtains tend to reduce perturbations of said at least one heated air curtain due to physical disturbances near said device when said canopy is raised above said support.

19. The combination infant radiant warmer and incubator thermal support device of claim 18 wherein said at least one heated curtain of air comprises a heated air curtain traveling from one of said head and foot ends of said support toward the other of said head and foot ends of said support and over an infant supported by said support.

20. The combination infant radiant warmer and incubator thermal support device of claim 18 wherein said at least one heated curtain of air comprises a heated air curtain traveling from one of said head and foot ends of said support toward the other of said head and foot ends of said support and over an infant supported by said support.

21. The combination infant radiant warmer and incubator thermal support device of claim 18 wherein said at least one heated curtain of air comprises:

a first heated air curtain traveling from one of said head and foot ends of said support toward the other of said head and foot ends of said support over an infant supported by said support; and second and third heated air curtains traveling from said lateral sides of said support upwardly and toward one another and over an infant supported by said support.

22. An infant thermal support device comprising:

a base;

an infant support mounted on said base;

a shelf storage area forming a part of said infant support; and a heater underlying said shelf storage area;

whereby infant treating accessories such as probes and the like can be stored on said shelf storage area and simultaneously kept warm such that when said accessories are placed in contact with the infant trauma of the infant is reduced.

23. An infant thermal support device comprising:

a base;

an infant support mounted on said base;

a transparent canopy mounted over said infant support; and a selectively controllable light shutter forming a part of said canopy;

whereby said shutter can be selectively controlled to permit ambient light to pass through and prevent ambient light from passing through said canopy.

24. An infant thermal support device comprising:

an infant support having head and foot ends and lateral sides;

at least one fan and at least one heater providing at least one heated curtain of air traveling over an infant on said support;

a fan providing curtains of air traveling upwardly from said lateral sides and at least one of said head and foot ends of said support;

a motion sensor mounted on said support for sensing disturbances around said device; and a controller responsive to said motion sensor for controlling the speed of said fan providing curtains of air traveling upwardly;

whereby said at least one heated air curtain provides warmth to the infant on said support and said upwardly oriented air curtains tend to reduce perturbations of said at least one heated air curtain due to physical disturbances near said device thus providing an infant thermal support device which does not require a canopy enclosing said device to maintain the infant warm, and whereby said controller, upon said sensor sensing a disturbance, is operable to increase the speed of said fan providing curtains of air traveling upwardly to further reduce perturbations of said at least one heated air curtain.

25. An infant thermal support device comprising:

an infant support having head and foot ends and lateral sides;

at least one fan and at least one heater providing at least one heated curtain of air traveling over an infant on said support;

a fan providing curtains of air traveling upwardly from said lateral sides and at least one of said head and foot ends of said support;

a canopy mounted over said support and adapted to be raised and lowered relative to said support;

a position sensor associated with said canopy for determining the position of said canopy relative to said support; and a controller responsive to said position sensor for controlling the speed of at least one of said fan providing curtains of air traveling upwardly and said at least one fan providing at least one heated air curtain;

whereby said at least one heated air curtain provides warmth to the infant on said support and said upwardly oriented air curtains tend to reduce perturbations of said at least one heated air curtain due to physical disturbances near said device thus providing an infant thermal support device which does not require said canopy to be lowered to enclose said support to maintain the infant warm, and whereby said controller, upon said sensor sensing the relative position of said canopy with respect to said support, is operable to decrease the speed of at least one of said fan providing curtains of air traveling upwardly as the need for those upwardly traveling curtains of air diminishes and said at least one fan providing at least one heated air curtain as the need for that heated air curtain diminishes due to said infant becoming substantially enclosed by said support and canopy.

26. The infant thermal support device of claim 25 wherein said controller is responsive to said position sensor for controlling the speed of said fan providing curtains of air traveling upwardly.

27. The infant thermal support device of claim 25 wherein said controller is responsive to said position sensor for controlling the speed of said at least one fan providing at least one heated air curtain.

28. The infant thermal support device of claim 25 wherein said controller is responsive to said position sensor for controlling the speed of said fan providing curtains of air traveling upwardly and the speed of said at least one fan providing at least one heated air curtain.

* * * * *